(12) United States Patent
Cintron et al.

(10) Patent No.: US 7,750,046 B2
(45) Date of Patent: *Jul. 6, 2010

(54) TREATMENT OF SYMPTOMS ASSOCIATED WITH IRRITABLE BOWEL SYNDROME

(75) Inventors: Lynn Cintron, Menlo Park, CA (US); Raymond R. Gaeta, Sunnyvale, CA (US)

(73) Assignee: The Board of Trustees of the Leland Stanford Jr. University, Palo Alto, CA (US)

( * ) Notice: Subject to any disclaimer, the term of this patent is extended or adjusted under 35 U.S.C. 154(b) by 1087 days.

This patent is subject to a terminal disclaimer.

(21) Appl. No.: 11/436,933

(22) Filed: May 15, 2006

(65) Prior Publication Data
US 2006/0205678 A1 Sep. 14, 2006

Related U.S. Application Data

(63) Continuation of application No. 10/291,204, filed on Nov. 8, 2002, now Pat. No. 7,045,549.

(60) Provisional application No. 60/338,093, filed on Nov. 8, 2001.

(51) Int. Cl.
*A61K 31/195* (2006.01)
(52) U.S. Cl. .................................................. 514/561
(58) Field of Classification Search ................ 514/716, 514/717, 576, 456, 454, 645, 561, 626, 651
See application file for complete search history.

(56) References Cited

U.S. PATENT DOCUMENTS

| 5,840,332 | A | 11/1998 | Lerner et al. |
|---|---|---|---|
| 5,900,233 | A | 5/1999 | Day |
| 5,965,557 | A | 10/1999 | Asano et al. |
| 6,127,418 | A | 10/2000 | Bueno et al. |
| 6,194,382 | B1 | 2/2001 | Crain et al. |
| 6,203,797 | B1 | 3/2001 | Perry |
| 6,228,040 | B1 | 5/2001 | Craine |
| 6,284,770 | B1 | 9/2001 | Mangel et al. |
| 6,297,226 | B1 | 10/2001 | Glasky |
| 6,653,314 | B2 * | 11/2003 | Cheng et al. ............... 514/256 |

FOREIGN PATENT DOCUMENTS

| WO | WO-00/50027 | 8/2000 |
|---|---|---|
| WO | WO 01/45684 | * 6/2001 |

OTHER PUBLICATIONS

Bueno et al., Am. J. Physiol. Gastrointest. Liver Physiol. (2000) 278:G670-G676.

Cintron and Gaeta, Abstracts from Society for Neuroscience (2000) 26:855.2.

(Continued)

*Primary Examiner*—Shengjun Wang
(74) *Attorney, Agent, or Firm*—Morrison & Foerster LLP (57) ABSTRACT

Methods are provided for use in treating humans suffering from irritable bowel syndrome. In the subject methods, an effective amount of a nerve-acting agent, e.g., lidocaine, topiramate, mexiletine and gabapentin, etc., is administered to a human suffering from irritable bowel syndrome. Also provided are pharmaceutical compositions and kits for use in practicing the subject methods.

5 Claims, 8 Drawing Sheets

VAS Pain Reduction With Lidocaine

OTHER PUBLICATIONS

Cintron and Gaeta, Neuropathic Agents in the Treatment of Chronic Abdominal Pain Due to Irritable Bowel Syndrome, poster presented Nov. 9, 2000.
Cintron et al., Abstracts, Int'l. Assoc. for the Study of Pain (2002) 146.
Elhakin et al., CA (2000) 132:303398.
Goodman and Gillman's 9th edition, Hardman et al. eds., McGraw-Hill, New York (1995) p. 157.
"Irritable Bowel Syndrome," Apr. 2003, NIH web site: http://digestive.niddk.nih.gov/ddieases/pubs/ibs.
Kralt et al., CA (1966) 65:89966.
Lundgren et al., CA (2000) 132:206290.
Martos et al., CA (1986) 105:146060.
Pace et al., Digestion (1995) 56:433-442.
Physicians' Desk Reference, 51st Edition (1997), MEXITIL p. 684.
Physicians' Desk Reference, 55th Edition (2001), TOPAMAX pp. 2392 and 2398.
Richekson et al., CA(1978) 90:145570.
Smith et al., CA (1937) 32:1329.
Takahiro, CA (1992) 121:99838.

* cited by examiner

TREATMENT OF SYMPTOMS ASSOCIATED WITH IRRITABLE BOWEL SYNDROME

CROSS-REFERENCE TO RELATED APPLICATIONS

This application is a continuation of U.S. patent application Ser. No. 10/291,204, filed 8 Nov. 2002, which claims the benefit of U.S. provisional application 60/338,093, filed 8 Nov. 2001. The contents of these documents are incorporated herein by reference.

FIELD OF THE INVENTION

The field of this invention is visceral pain, i.e., Irritable Bowel Syndrome, and the treatment thereof.

BACKGROUND OF THE INVENTION

Visceral pain affects the viscera, such as the intestines. One common type of visceral pain is Irritable Bowel Syndrome (IBS). IBS is a functional bowel disorder in which abdominal pain is associated with defecation or a change in bowel habits. IBS has elements of an intestinal motility disorder, a visceral sensation disorder, and a central nervous disorder. While the symptoms of IBS have a physiological basis, no clear mechanism unique to IBS has been identified. Rather, the same mechanisms that cause occasional abdominal discomfort in healthy individuals seem to operate to produce the symptoms of IBS. The symptoms of IBS are therefore a product of quantitative differences in the motor reactivity of the intestinal tract, and increased sensitivity to stimuli or spontaneous contractions.

Due to a lack of a readily identifiable structural or biochemical abnormality in this syndrome, the medical community has developed a consensus definition and criteria, known as the Rome criteria, to aid in diagnosis of IBS. According to the Rome criteria, IBS is indicated by abdominal pain or discomfort which is (1) relieved by defection and/or (2) associated with a change in frequency or consistency of stools, plus two or more of the following altered stool frequency, altered stool formation, altered stool passage, passage of mucus, and bloating or feeling of abdominal distention (Dalton, C. and Drossman, D. A., Am Fam Physician 1997 55(3): 875-880). Thus, a hallmark of IBS is abdominal pain that is relieved by defecation, and which is associated with a change in the consistency or frequency of stools. IBS may be diarrhea-predominant, constipation-predominant, or an alternating combination of both.

Persons with IBS exhibit hypersensitivity, particularly hyperalgesia (increased response to a painful stimulus), in response to painful distensions in the small bowel and colon and to normal intestinal function. Furthermore, there are also increased or unusual areas of visceral pain. The abdominal pain is often poorly localized, and may be migratory and/or variable in nature. The pain may be worsened by meals and reduced upon defecation. Furthermore, IBS symptoms, including hyperalgesia, are commonly initiated or exacerbated by stress (Dalton, C. and Drossman, D. A., Am Fam Physician 1997 55(3):875-880).

IBS is estimated to affect up to 20% of the adult population worldwide. Women apparently are more often affected than men, and the prevalence of Irritable Bowel Syndrome is lower among the elderly (Camilleri, M. and Choi, M. G., Aliment Pharmacol Ther 1997 11(1):3-15). It also seems clear that psychological factors, either stress or overt psychological disease, modulate and exacerbate the physiological mechanisms that operate in IBS (Drossman, D. A. et al., Gastroenterology 1988 95:701-708).

Some studies suggest that only about 10% to 50% of those afflicted with IBS actually seek medical attention. Nonetheless, IBS still accounts for up to about 3.5 million physician visits per year, and is the most common diagnosis in a gastroenterologists' practice, accounting for about 25% of all patients (Camilleri and Choi, 1997). In a study published in 1993, persons afflicted with IBS were found to have more frequent doctor visits, a lower quality of life, and to miss three times as many days from work as those with no bowel symptoms (Drossman, D. A., Dig Dis Sci 1993 38:1569-1580). As a consequence, persons with IBS incur higher health care costs than those without IBS (Talley, N. J. et al., Gastroenterology 1995 109:1736-1741).

Attempts to treat IBS generally focus on either (1) treatments directed to the intestinal tract (so-called "end organ therapy") or (2) treatments directed to affective disorders mediated by the CNS which are associated with IBS (Farthing, M. J. G. Drugs 1998 56(1):11-21). Among the former are gut transit accelerants, such as wheat bran, soluble fiber, and polycarbophil calcium, for constipation-predominant IBS; antidiarrheals, such as loperamide, diphenoxylate, and codeine phosphate, for diarrhea-predominant IBS; and anticholinergics and smooth muscle relaxants, such as cimetropium bromide, pinaverium bromide, octilium bromide, trimebutine, and mebeverine, for diarrhea-predominant IBS and abdominal pain. In addition, alterations in diet have been targeted for those patients with food sensitivities or food allergies.

The end organ therapy treatments for IBS have proved minimally effective or contain inherent drawbacks that limit their usefulness. For example, while the gut accelerants are useful to accelerate gut transit, they also exacerbate abdominal pain and bloating. Likewise, while antidiarrheals, such as loperamide, are often effective in treating diarrhea-predominant IBS, they are ineffective in treating the additional symptoms associated with IBS, such as abdominal pain. As a consequence, end organ therapy often is limited to patients with mild or moderate symptoms.

The anticholinergics and smooth muscle relaxants are effective in relieving pain associated with IBS, although their effects on other symptoms associated with IBS is unclear (Committee, Gastroenterology 1997 112:2120-2137; Pace, F. et al., Digestion 1995 56:433-442). In addition, some of the most effective compounds in these classes are not available for use in the United States, since they have not been approved by the Federal Food and Drug Administration (Committee, 1997). Finally, dietary alterations are of limited utility for a small segment of IBS patients.

Central nervous system treatments have received attention as potential IBS therapies. The tricyclic antidepressants, such as amitriptyline, imipramine, and doxepin, are frequently used to treat IBS, due to the neuromodulatory and analgesic properties of these compounds, which are independent of their psychotropic effects. However, because of their psychotropic properties, administration of these drugs requires long-term care, and is usually only given to patients with severe or refractory symptoms, impaired daily function, or associated depression or anxiety attacks. Furthermore, the newer antidepressants, in particular serotonin (5HT3) reuptake inhibitors, such as fluoxetine, sertraline, and paroxetine, have not been shown to be more effective than the tricyclic antidepressants (Committee, 1997). Conversely, 5HT3 inhibitors are used for relief of diarrhea prone IBS. Unfortunately, significant morbidity and mortality has been reported.

There remains continued interest in identifying new methods for treating IBS.

RELEVANT LITERATURE

U.S. Patents of interest include: U.S. Pat. Nos. 6,284,770; 6,228,040; 6,203,797; 6,194,382; 5,965,557; 5,900,233; 5,840,332; 6,127,418; and 6,297,226.

SUMMARY OF THE INVENTION

Methods are provided for use in treating humans suffering from visceral pain, e.g. irritable bowel syndrome. In the subject methods, an effective amount of a nerve-acting agent, e.g., lidocaine, topiramate, mexiletine or gabapentin, is administered to a human suffering from irritable bowel syndrome. Also provided are pharmaceutical compositions and kits for use in practicing the subject methods.

FEATURES OF THE INVENTION

The subject invention provides method of treating a human with Irritable Bowel Syndrome by administering to said human an effective amount of a nerve-acting agent. In certain embodiments, the nerve-acting agent is an agent that attenuates visceral nerve signals. In certain embodiments, the nerve-acting agent is a frequency dependant sodium channel blocker (e.g., lidocaine, topiramate and mexiletine, etc.). In certain embodiments, the nerve-acting agent is selected from the group of agents known in the art as anti-convulsant agents. In certain embodiments, the nerve-acting agent is gabapentin or an analog thereof. In certain embodiments, the nerve-acting agent is administered systemically. In certain embodiments, the nerve-acting agent is administered orally. In certain embodiments, the nerve-acting agent is administered intravenously, transdermally, topically, or by intraspinal, intrathecal, epidural, intra-cerebral, intraventricular, inhalational, per-rectal, intravaginal, nasal, buccal, intra-muscular, intradermal, intra-peritoneal, per-NGT, intra arterial, or sublingual means.

Typically, the nerve-acting agent is administered as a pharmaceutical preparation. In certain embodiments, the method further includes administering an effective amount of a non-nerve-acting irritable Bowel Syndrome agent.

Also provided are kits for use in treating a human for Irritable Bowel Syndrome according to the subject methods, where the kits include an effective amount of a nerve-acting agent, and instructions for use in treating a human for Irritable Bowel Syndrome by administration of said nerve-acting agent. In certain embodiments, the kits also include an effective amount of a non-nerve-acting Irritable Bowel Syndrome agent, which agent may be present in a pharmaceutical composition that also includes the nerve-acting agent.

Also provided are pharmaceutical preparations that include a nerve-acting agent in an oral amount ranging from about 0.001 to about 10,000 (mcg, mg, gm, %, mg/dl, mcg/ml, international units (IU), ml/hr, mcg/hr, mg/kg/hr, mg/kg/min, mcg/kg/hr, mcg/kg/min, picograms, nanograms, or milliequivalants) present in a pharmaceutically acceptable vehicle, where such compositions are specifically tailored for use in the subject methods, and may include an additional non-nerve-acting IBS treatment agent.

DESCRIPTION OF THE SPECIFIC EMBODIMENTS

Methods are provided for use in treating humans suffering from Irritable Bowel Syndrome. In the subject methods, an effective amount of a nerve-acting agent, e.g., lidocaine, topiramate, mexiletine and gabapentin, etc., is administered to a human suffering from Irritable Bowel Syndrome. Also provided are pharmaceutical compositions and kits for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the components which are described in the publications which might be used in connection with the presently described invention.

As summarized above, the subject invention provides methods of treating a human subject suffering from Irritable Bowel Syndrome, as well as pharmaceutical preparations and kits for use in practicing the subject methods. Each of these components is now described in greater detail below.

This invention pertains to the discovery that nerve-acting agents are effective for ameliorating or treating Irritable Bowel Syndrome in a human. Irritable Bowel Syndrome or "IBS" is defined above. The human patient, subject or host that is treated with the subject methods may be male or female, and may be any age, e.g., a child or adult. The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation. By "treatment" is meant at least an amelioration of at least one of the symptoms associated with the disease condition afflicting the host, where amelioration is used in a broad sense to refer to at least a reduction in the magnitude of a parameter, e.g. symptom, associated with the pathological condition being treated, such as bloating and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In practicing the subject methods, an effective amount of a nerve-acting agent is administered to a human subject diagnosed or suspected of having IBS. The subject may be diagnosed to have IBS using any convenient protocol, including the diagnostic protocols described in U.S. Pat. Nos. 6,284,770; 6,228,040; 6,203,797; 6,194,382; 5,965,557; 5,900,233; the disclosures of which are herein incorporated by reference Nerve-acting agents of interest that find use in the subject methods are, in many embodiments, agents that attenuate visceral nerve signals and/or decrease neuronal activity when administered to the subject. Representative agents of interest include, but are not limited to: local anesthetics; anticonvulsants; and the like. Local anesthetic agents of interest include, but are not limited to: lidocaine, ropivicaine, bupivicaine, butamben, butanilicaine, ethyl aminobenzoate, fornocaine, hydroxyprocaine, isobutyl aminobenzoate, naepaine, octacaine, parethoxycaine, piridocaine, prilocaine, procaine, risocaine, tolycaine, trimecaine, ethylaminobenzoate (benzocaine), etc. Also of interest are anticonvulsants. Anticonvulsants of interest include, but are not limited to: lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphetnylan and L-5-hydroxytryptophan. In certain embodiments, sodium channel blockers are of interest, e.g., lidocaine, topiramate, and mexiletine, where the agent is not gabapentin or an analog thereof. In other embodiments, the agent is gabapentin or an analog thereof, e.g., 1-aminomethyl-3-methylcyclohexyl)acetic acid, (1-aminomethyl-3-methylcyclopentyl)acetic acid, and (1-aminomethyl-3,4-dimethylcyclopentyl)acetic acid, etc.

In the methods of the subject invention, an effective amount of the active agent(s) is administered to the subject, where "effective amount" means a dosage sufficient to produce the desired result, e.g., an improvement in a disease condition or the symptoms associated therewith of the IBS condition being treated, e.g., bloating, pain, etc. The active agent may be administered to the host using any convenient means capable of producing the desired result. Thus, the active agent can be incorporated into a variety of formulations for therapeutic administration. More particularly, the active agent of the present invention can be formulated into pharmaceutical compositions by combination with appropriate, pharmaceutically acceptable carriers or dilutents, and may be formulated into preparations in solid, semi-solid, liquid or gaseous forms, such as tablets, capsules, powders, granules, ointments, solutions, suppositories, injections, inhalants and aerosols. As such, administration of the active agent can be achieved in various ways, including oral, buccal, rectal, parenteral, intraperitoneal, intradermal, transdermal, intracheal, etc., administration. In pharmaceutical dosage forms, the active agent may be administered alone or in combination with other pharmaceutically active compounds. The following methods and excipients are merely exemplary and are in no way limiting.

For oral preparations, the active agent can be used alone or in combination with appropriate additives to make tablets, powders, granules or capsules (including sustained released formulations), for example, with conventional additives, such as lactose, mannitol, corn starch or potato starch, with binders, such as crystalline cellulose, cellulose derivatives, acacia, corn starch or gelatins, with disintegrators, such as corn starch, potato starch or sodium carboxymethylcellulose; with lubricants, such as talc or magnesium stearate; and if desired, with diluents, buffering agents, moistening agents, preservatives and flavoring agents.

The active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The active agent can be utilized in aerosol formulation to be administered via inhalation. The compounds of the present invention can be formulated into pressurized acceptable propellants such as dichlorodifluoromethane, propane, nitrogen and the like. Furthermore, the active agent can be made into suppositories by mixing with a variety of bases such as emulsifying bases or water-soluble bases The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unfit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Details on techniques for formulation and administration are well described in the scientific and patent literature, see, for example, the latest edition of "Remington's Pharmaceutical Sciences" (Maack Publishing Co, Easton Pa.).

Representative specific formulations are provided for representative drugs in the Experimental Section, below.

The methods of the invention ameliorate IBS, i.e., prevent, slow the onset of, decrease the frequency of, diminish the severity of or cure IBS and/or its complications. The amount of active agent adequate to accomplish this result is defined as a "therapeutically effective dose." The dosage schedule and amounts effective for this use, i.e., the "dosing regimen," will depend upon a variety of factors, including the stage of the disease or condition, the severity of the disease or condition, then patient's physical status, age and the like. In calculating the dosage regimen for a patient, the mode of administration, also is taken into consideration. The dosage regimen must also take into consideration the pharmacokinetics, i.e., the active agent's rate of absorption, bioavailability, metabolism, clearance, and the like (see, for example, Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. As an illustrative example, the guidelines provided below for the specific representative active agents of the experimental section can be used as guidance to determine the dosage regiment, i.e., dose schedule and dosage levels, of any active agent administered when practicing the methods of the invention.

Single or multiple administrations of the active agent formulations may be administered depending on the dosage and frequency as required and tolerated by the patient. In certain embodiments, the amount of active agent employed in pharmaceutical preparations useful for the subject invention range from about 0.001 to about 10,000 mcg. In certain embodiments, the amount of active agent employed in pharmaceutical preparations useful for the subject invention range from about 0.001 to about 10,000 mg. In certain embodiments, the amount of active agent employed in pharmaceutical preparations useful for the subject invention range from about 0.001 to about 10,000 gm. In certain embodiments, the amount of active agent employed in pharmaceutical preparations useful for the subject invention range from about 0.001 to about 10,000%. In certain embodiments, the amount of active agent employed in pharmaceutical preparations useful for the subject invention range from about 0.001 to, about 10,000 mg/dl. In certain embodiments, the amount of active agent employed in pharmaceutical preparations useful for the subject invention range from about 0.001 to about 10,000 mcg/ml. In certain embodiments, the amount of active agent employed in pharmaceutical preparations useful for the subject invention range from about 0.001 to about 10,000 international units (IU). In certain embodiments, the amount of active agent employed in pharmaceutical preparations useful for the subject invention range from about 0.001 to about 10,000 ml/hr. In certain embodiments, the amount of active agent employed in pharmaceutical preparations useful for the subject invention range from about 0.001 to about 10,000 mcg/hr. In certain embodiments, the amount of active agent employed in pharmaceutical preparations useful for the subject invention range from about 0.001 to about 10,000 mg/kg/hr. In certain embodiments, the amount of active agent employed in pharmaceutical preparations useful for the subject invention range from about 0.001 to about 10,000 mg/kg/min. In certain embodiments, the amount of active agent employed in pharmaceutical preparations useful for the subject invention range from about 0.001 to about 10,000 mcg/kg/hr. In certain embodiments, the amount of active agent employed in pharmaceutical preparations useful for the subject invention range from about 0.001 to about 10,000 mcg/kg/min. In certain embodiments, the amount of active agent employed in pharmaceutical preparations useful for the subject invention range from about 0.001 to about 10,000 picograms. In certain embodiments, the amount of active agent employed in pharmaceutical preparations useful for the subject invention range from about 0.001 to about 10,000 nanograms. In certain embodiments, the amount of active agent employed in pharmaceutical preparations useful for the subject invention range from about 0.001 to about 10,000 milliequivalants.

The formulations should provide a sufficient quantity of active agent to effectively ameliorate the IBS condition. Thus, a typical pharmaceutical formulation for oral administration of gabapentin would be about 0.5 to about 25.0, often from about 1.0 to 20.0 mg/kg of body weight per patient per day, e.g., 1.42 to about 17.14 mg/kg of body weight per patient per day. Oral mexiletine doses range from 0.5 to about 25.0, often from about 1.0 to 15.0 mg/kg of body weight per patient per day, e.g. 1.14 to 12.85 mg/kg. Oral topiramate dosages range from 0.1 to about 10.0, often from about 0.2 to 5.0 mg/kg of body weight per patient per day, e.g., 0.35 to 2.85 mg/kg. Lower dosages of these agents may be used, particularly when the drug is administered to an anatomically secluded site, such as the cerebral spinal fluid (CSF) space, in contrast to administration orally, into the blood stream, into a body cavity or into a lumen of an organ. Substantially higher dosages are possible in topical administration. Actual methods for preparing parenterally administrable active agent formulations will be known or apparent to those skilled in the art and are described in more detail in such publications as Remington's Pharmaceutical Science, 15th ed., Maack Publishing Company, Easton, Pa. (1980). In a preferred embodiment of the invention, the invention provides for a method of treating IBS by administering active agent in a daily amount of about 0.1 to 25.0 mg/kg, e.g., from about 0.35 to about 17.14 mg per kilogram of body weight per day. Using this dosage, the administration can continue for a period of about 30 to 90 days.

After a pharmaceutical comprising an active agent of the invention has been formulated in an acceptable carrier, it can be placed in an appropriate container and labeled for treatment of an indicated condition. For administration of active agents, such labeling would include, for example, instructions concerning the amount, frequency and method of administration. In one embodiment, the invention provides for a kit for the amelioration of psychosis in a human, which includes an active agent and instructional material teaching the indications, dosage and schedule of administration of the active agent.

In certain embodiments, the methods further included administration of an effective amount of a non-nerve-acting agent which also imparts relief from IBS or symptoms thereof, where such agents include: wheat bran, soluble fiber, and polycarbophil calcium, for constipation-predominant IBS; antidiarrheals, such as loperamide, diphenoxylate, and codeine phosphate, for diarrhea-predominant IBS; and anticholinergics and smooth muscle relaxants, such as cimetropium bromide, pinaverium bromide, octilium bromide, trimebutine, and mebeverine, for diarrhea-predominant IBS and abdominal pain; tricyclic antidepressants, such as amitriptyline, imipramine, and doxepin; specific serotonin reuptake inhibitors, such as fluoxetine, serraline, and paroxetine; and the like.

Such agents may be administered as a separate composition or in the same composition as the nerve-acting agent as described above.

As indicated above, the subject invention provides for at least amelioration of IBS symptoms. For example, in certain embodiments, the subject invention provides for a reduction in visceral pain of at least about 50%, usually at least about 33% and more usually at least about 25%, as measured using the assay described in the experimental section, below. Likewise, in certain embodiments the subject invention provides for a reduction in bloating of at least about 50%, usually at least about 33% and more usually at least about 25%, as determined using the assay described in the experimental section, below.

Kits with unit doses of the active agent(s), usually in oral or injectable doses and often in a storage stable formulation, are provided. Preferred compounds and unit doses are those described herein above. In such kits, in addition to the containers containing the unit doses will be an informational package insert describing the use agent(s) in treating IBS. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e g., diskette, CD, etc., on which the information has been recorded. Yet another means that may be present is a website address which may be used via the Internet to access the information at a removed site. Any convenient means may be present in the kits.

The following examples are offered by way of illustration, and not by way of limitation.

EXPERIMENTAL

I. Introduction

This study assesses the use of nerve-acting drugs for the treatment of visceral pain, such as Irritable Bowel Syndrome (IBS). Common symptoms in IBS, such as diarrhea, constipation or abdominal pain and bloating are not currently well explained by any structural or biochemical abnormality. Drugs selected for this study, i.e. lidocaine, mexiletine and topiramate, all have some degree of sodium channel blocking activity. Gabapentin (Neurontin) has a less defined mechanism in decreasing irritable nerve signals. Possible mechanisms include selective depression of spinal cord pain transmission and reducing discharge of tonically active peripheral nerve fibers.

II. Methods

This is a longitudinal single blinded, randomized placebo controlled study in which patients act as their own controls. Subjects were volunteers who met the Rome Criteria for IBS and without other active bowel disease (i.e. GERD, colon cancer). Both adult men and women participated, ranging in age from 23 to 75 years old, with greater number of women by a ratio of 2.5:1. Subjects responded to a Bowel Symptom Questionnaire (B. Naliboff, UCLA) as well as a Brief Mood Survey (D. Burns, Stanford). Baseline questionnaire results were taken just prior to any drug treatment as well as shortly after. In addition, data was collected during a washout period of one week without any study drug. Drugs studied included intravenous lidocaine and a trial of the oral mexiletine, topiramate, gabapentin or placebo.

A titration period of three to four weeks is being used to stabilize each patient on an efficacious dose of medication. Oral mexiletine (daily dose 300 to 900 mg), topiramate (daily dose 15 to 100 mg) and gabapentin (daily dose of 300 to 900 mg per day) and a placebo were taken in syrup that was blinded to the patient. During each week of the titration period, the cocktail was modified to allow a gradual increase or decrease in dose. Results were collected weekly by questionnaires.

Benefit in treating chronic IBS using nerve-acting agents was quantified by a decrease in mean values of abdominal pain with a 20-point Visual Analogue scale and a decrease in bowel symptoms (bloating, etc.) using a 20-point scale. Mood was also followed by a Brief Mood Survey, which rates Depression, Anxiety, Panic, Anger and Suicidal Urge (88 points maximum total).

III. Results

Figure 1:
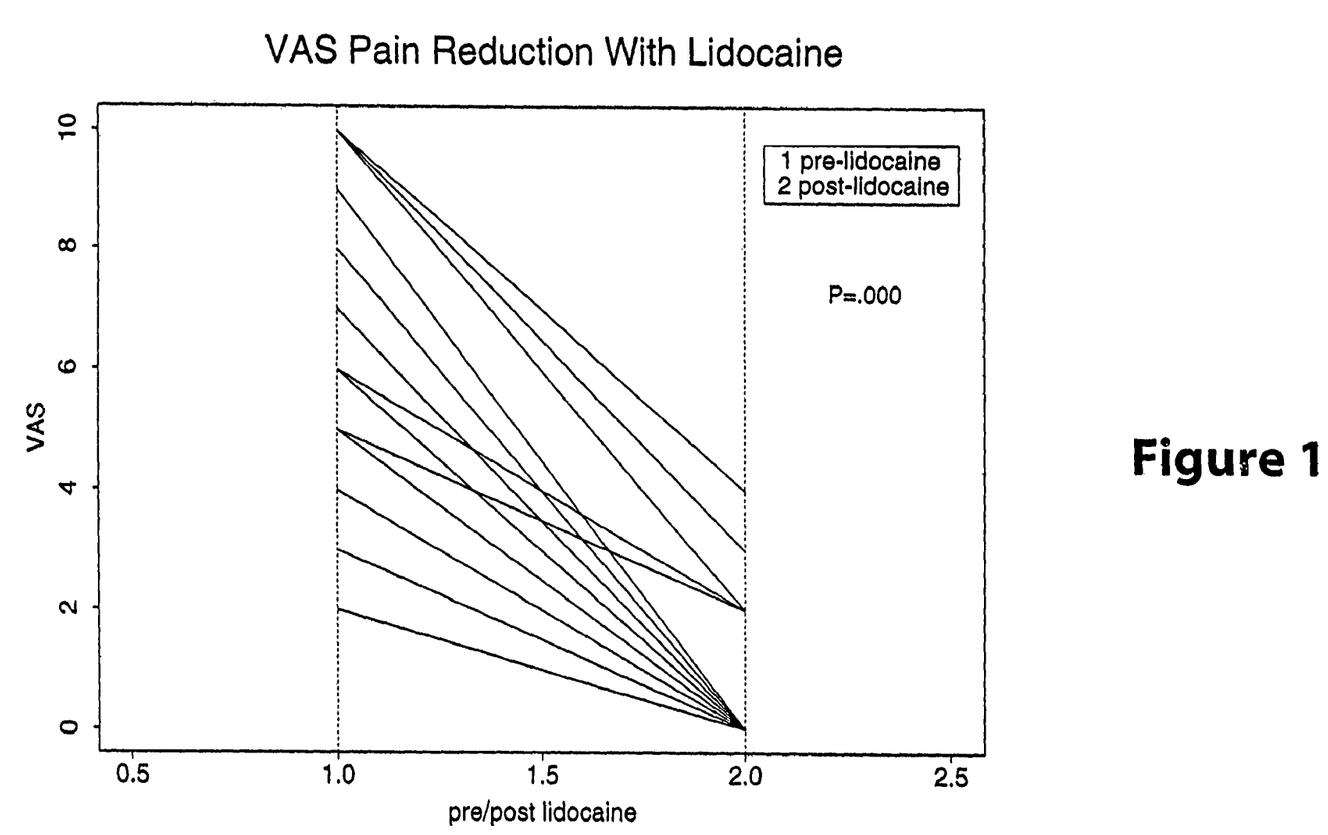
FIGS. 1 to 8 provide graphical results of various experiments reported in the experimental section below.
Figure 2:
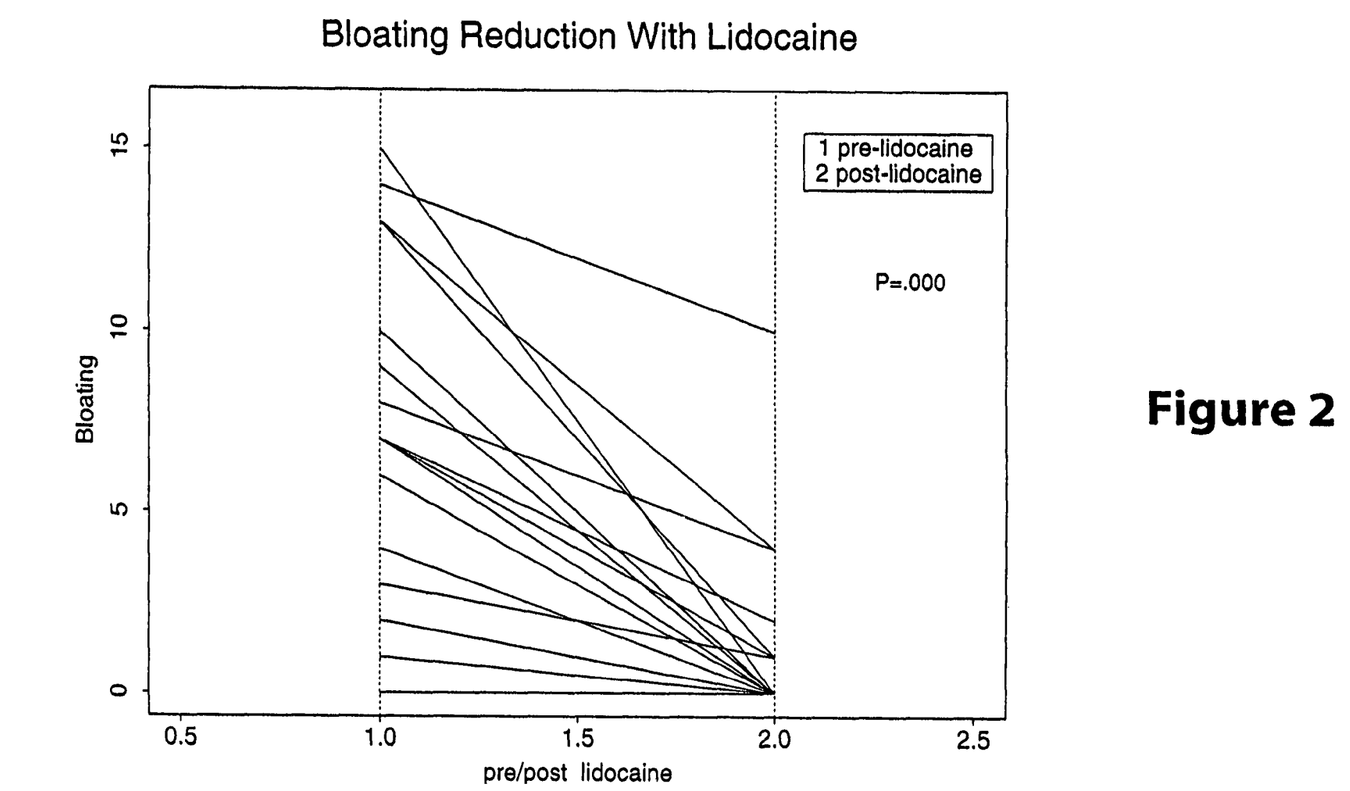
Figure 3:
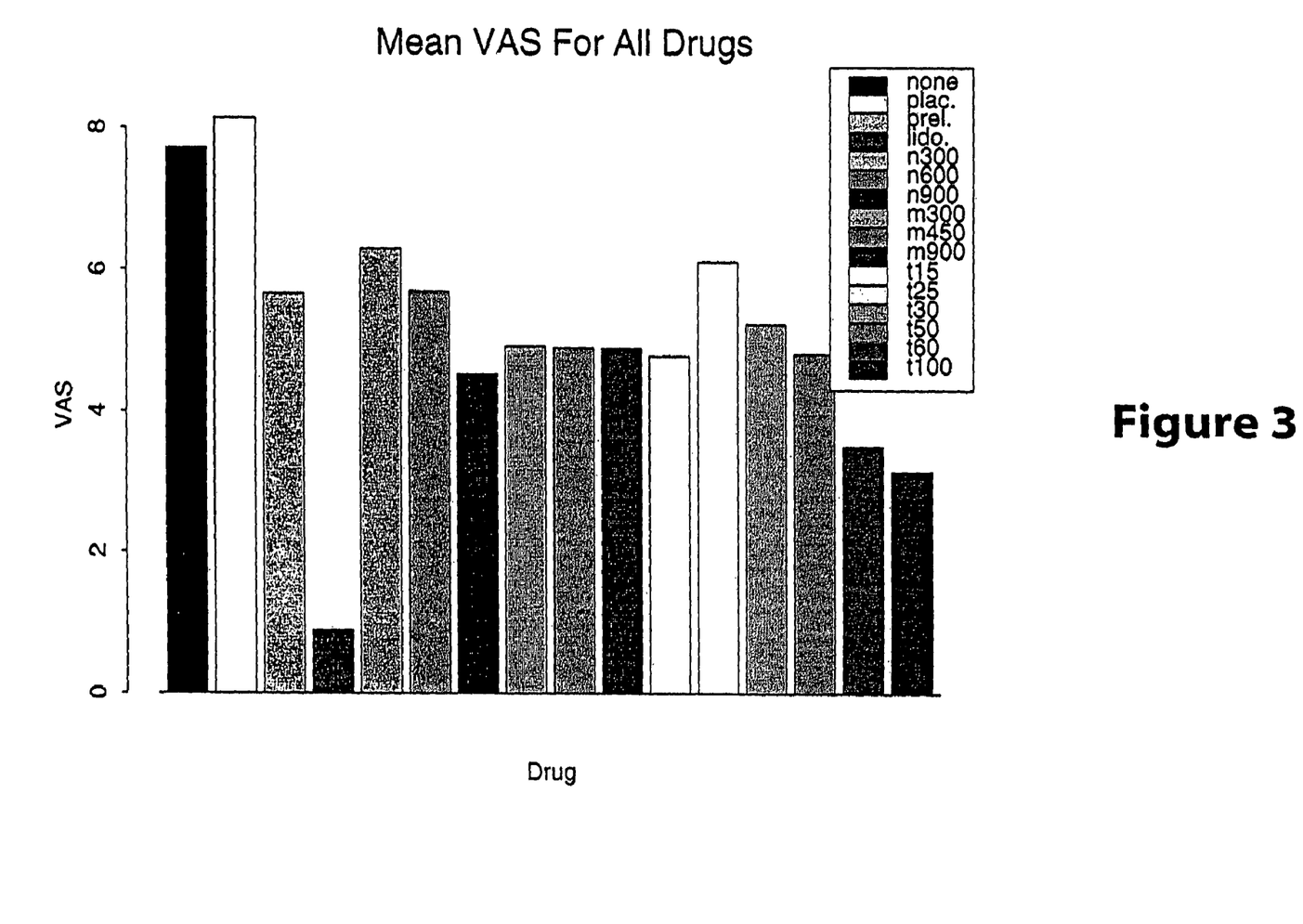
Figure 4:
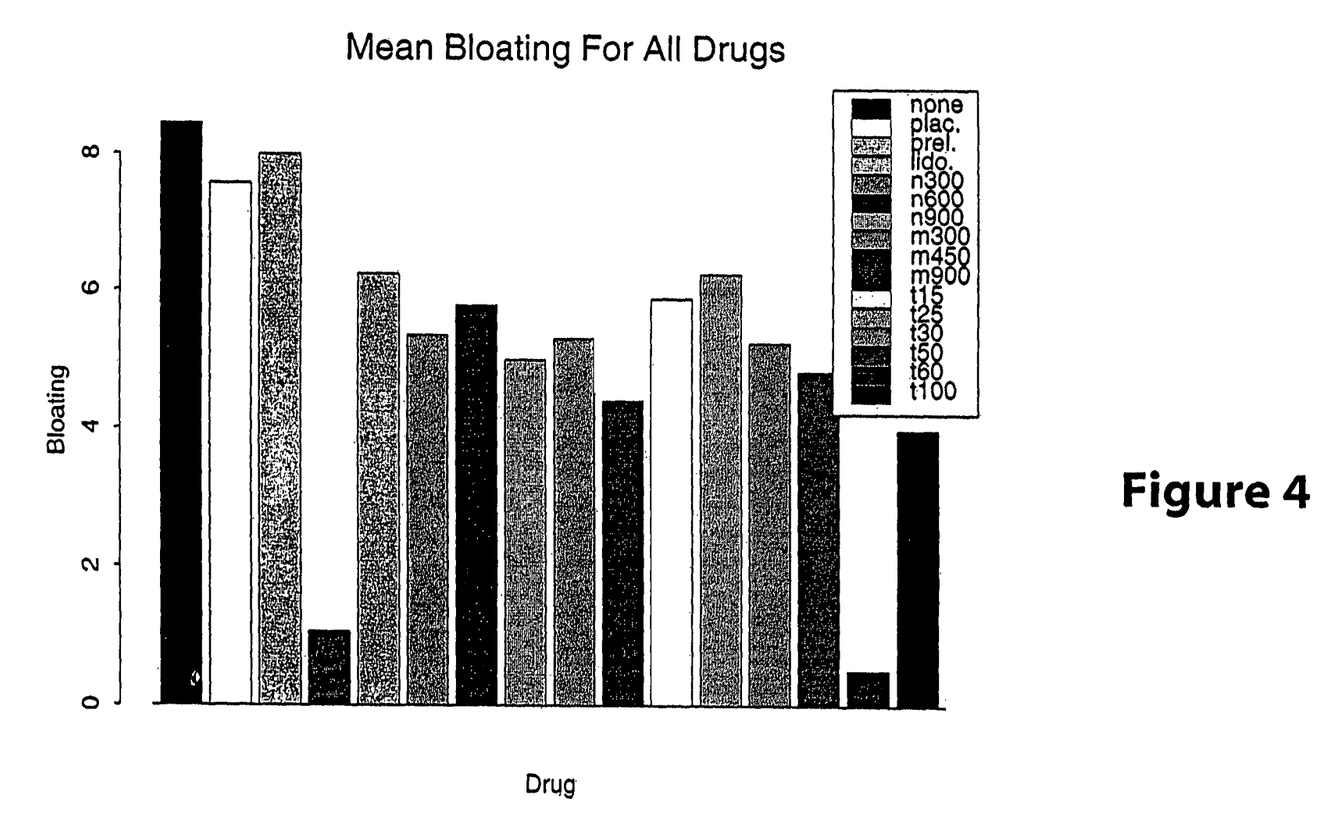

The impact of intravenous lidocaine on abdominal pain and bloating appeared significant in 22 subjects thus far. All patients had a significant drop in their scores. VAS Pain scores (20 point scale) showed a mean reduction of 4.80 and a p-value of 0.000 (FIG. 1). Bloating showed a mean reduction of 6.8 and a p-value of 0.000 (FIG. 2). Results from the oral drugs revealed a general decrease in mean VAS abdominal and bloating (20 point) scores, although less significant (FIGS. 3 & 4).

Figure 5:
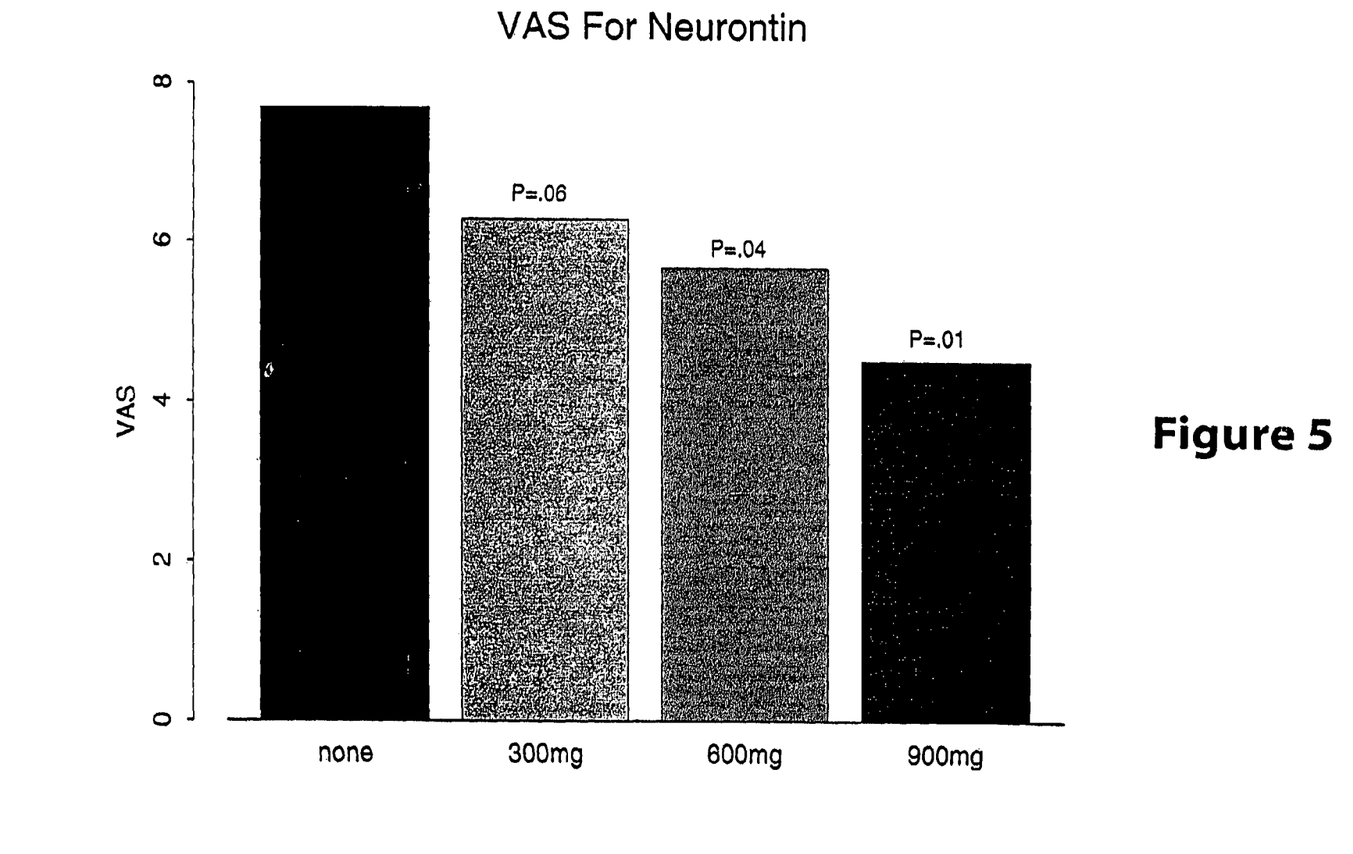
Figure 6:
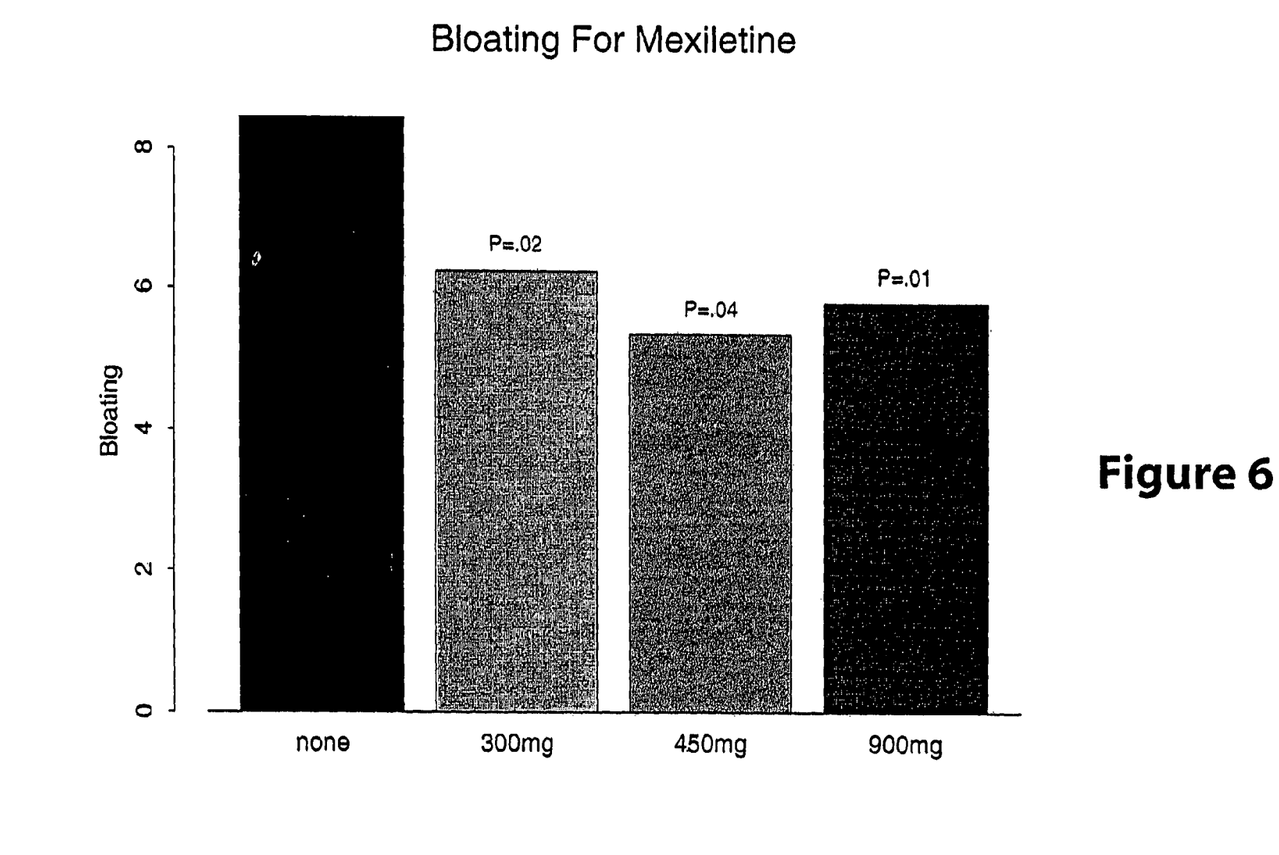
Figure 7:
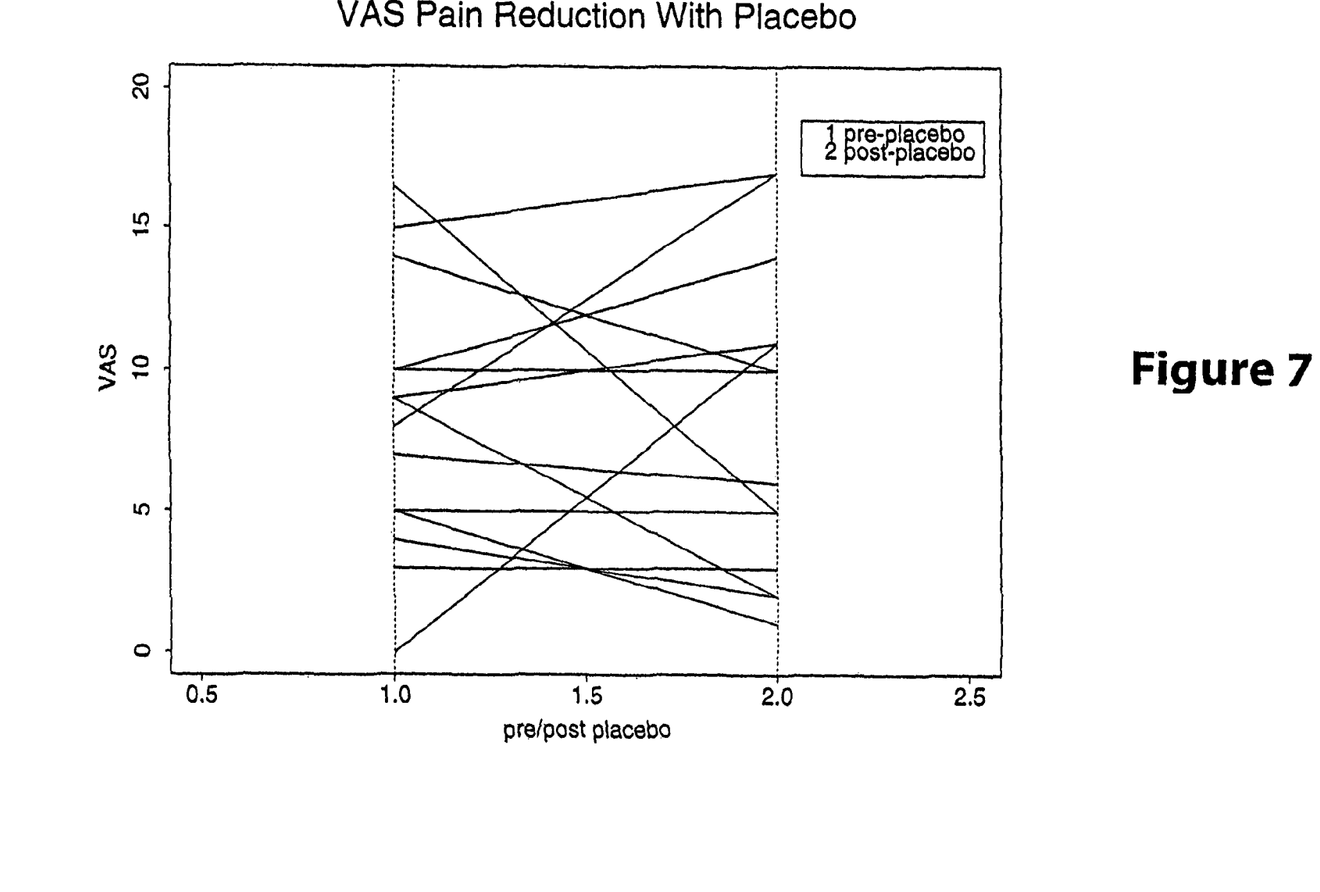
Figure 8:
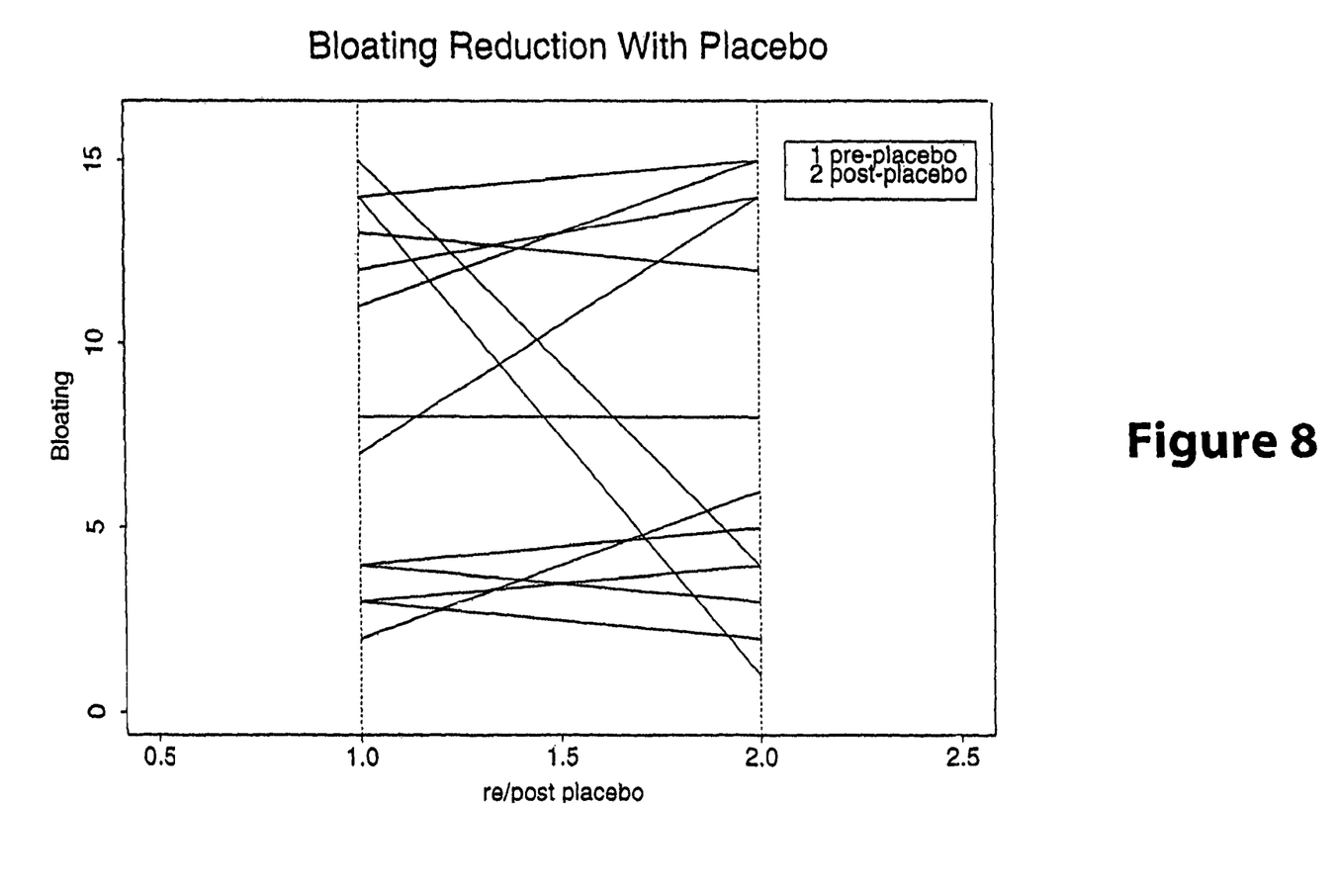

For gabapentin (Neurontin) there was a drop in mean VAS pain scores with a p-value of increasing significance as dosage increased from 300 to 600 to 900 mg ($p=0.06, 0.04$ &. 01) (FIG. 5). Mexiletine also showed significant results in decreasing bloating, in fact, at all dosages 300 mg, 450 mg & 900 mg; $p=0.02, 0.04$ & 0.01)(FIG. 6). Of particular interest, the placebo did not seem to reduce VAS pain or bloating significantly (FIGS. 7 & 8) compared to all study drugs. Side effects reported were sedation and tongue numbness, which resolved after drug was discontinued. Two subjects reported fatigue on topiramate 25 mg qhs, which also resolved after discontinuation.

In further analysis, where Ho (Null Hypothesis) is no reduction of symptom versus H1, which is some reduction, the following was noted:

Placebo does not seem to reduce VAS or bloating significantly, but it does influence the mood, through placebo effect.

Lidocaine is the most influential drug of all, highly significant for VAS, bloating and mood.

Effects of gabapentin become more pronounced as the dosage is increased.

Effects of mexiletine are significant at all dosages.

Topiramate has the least effect of all drugs. The effects barely become significant at doses of 50 mg and higher.

Test for the difference in sexes was not significant.

In assessing whether Ho means the drug effect is equal to placebo effect and H1 is where drug has more effect than placebo, the following was noted:

All the drugs have similar effect on the mood as placebo and differ from it (for mood) only at highest doses.

Lidocaine has much stronger effect than placebo.

Gabapentin is different from placebo at doses 600 mg and higher.

Mexiletine is different from placebo at all levels for VAS and bloating.

Topiramate is different from placebo for VAS and bloating at doses 50 mg and higher.

In addition, regression analysis to determine if the score depends on drug dosage. The following findings were made:

Larger doses of gabapentin & mexiletine have some effect on VAS & bloating. This is especially true for mexiletine. Both are not very important for mood.

Larger doses of topiramate do not significantly reduce any score in a predictable manner, although 60 mg showed a borderline effect on decreasing bloating.

IV. Conclusion

Intravenous lidocaine appears to be very effective in immediately relieving symptoms of abdominal pain, bloating and distension in IBS. The data indicated that lidocaine and oral nerve-acting drugs are beneficial treatments for relief of visceral pain and symptoms as seen in Irritable Bowel Syndrome. Their effect may relate to attenuation of excess activity of visceral nerves as well as brain-gut pathways, even at low therapeutic doses. Oral nerve-acting agents also play a role in improving improve pain, bowel symptoms & mood at lower therapeutic dosages. The novel use of such drugs has potential for future pharmaceutical design.

It is evident from the above discussion and results that the subject invention provides an effective new way of treating irritable bowel syndrome. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of alleviating bloating in a human with irritable bowel syndrome (IBS), said method comprising:
    a) identifying a human experiencing bloating due to IBS;
    b) administering to said human an effective amount of an agent which is gabapentin or an analog thereof;
    whereby said bloating due to IBS is alleviated.

2. The method of claim 1, wherein said agent is administered intravenously.

3. The method of claim 1, wherein said agent is administered orally.

4. The method of claim 1, wherein said agent is administered transdermally.

5. The method of claim 1, wherein said method further comprises administering an effective amount of a non-nerve-acting irritable bowel syndrome agent.

* * * * *